United States Patent
Chai et al.

(10) Patent No.: US 6,706,483 B1
(45) Date of Patent: Mar. 16, 2004

(54) METHOD OF IDENTIFYING AND TREATING INVASIVE CARCINOMAS

(75) Inventors: Karl X. Chai, Winter Springs, FL (US); Li-Mei Chen, Winter Springs, FL (US); Lee Chao, Mr. Pleasant, SC (US); Julie Chao, Mr. Pleasant, SC (US)

(73) Assignee: University of Central Florida, Orlando, FL (US)

( * ) Notice: Subject to any disclaimer, the term of this patent is extended or adjusted under 35 U.S.C. 154(b) by 0 days.

(21) Appl. No.: 10/368,750

(22) Filed: Feb. 18, 2003

Related U.S. Application Data

(62) Division of application No. 09/755,811, filed on Jan. 5, 2001, now Pat. No. 6,569,684.
(60) Provisional application No. 60/174,801, filed on Jan. 6, 2000.

(51) Int. Cl.[7] .......................... C12Q 1/68; G01N 33/48; C07H 21/02

(52) U.S. Cl. .................. 435/6; 536/23.1; 536/23.2; 536/23.5; 436/64

(58) Field of Search .................. 429/9.1, 184.1, 429/185.1, 277.1, 94.1, 94.64; 435/6, 325; 436/64; 514/1; 530/350; 536/23.1, 23.2, 23.5

(56) References Cited

U.S. PATENT DOCUMENTS

| | | | |
|---|---|---|---|
| 5,686,419 A | 11/1997 | Powers et al. | 514/18 |
| 5,871,917 A | 2/1999 | Duffy | 435/6 |
| 6,043,033 A | 3/2000 | Bandman et al. | 435/6 |
| 6,048,970 A | 4/2000 | Lal et al. | 536/23.5 |
| 6,075,136 A | 6/2000 | Tang et al. | 536/23.1 |
| 6,090,559 A | 7/2000 | Russell et al. | 435/6 |
| 6,090,786 A | 7/2000 | Augustyns et al. | 514/19 |
| 6,107,049 A | 8/2000 | Allard et al. | 435/7.1 |
| 6,303,318 B1 | 10/2001 | O'Brien | 435/7.1 |
| 6,335,170 B1 * | 1/2002 | Orntoft | 435/6 |
| 6,645,734 B2 | 11/2003 | Kominami | 435/7.95 |
| 2002/0052308 A1 * | 5/2002 | Rosen et al. | 514/1 |

OTHER PUBLICATIONS

Akazaki K. Stemmerman GN. Comparative study of latent carcinoma of the prostate among Japanese in Japan and Hawaii. Journal of the National Cancer Institute. 50(5):1137–44, 1973.

Berteau P. Laribi A. Eschwege P. Lebars I. Dumas F. Benoit G. Loric S. Prostasin mRNA to detect prostate cells in blood of cancer patients. Clinical and Chemical Laboratory Medicine 37 (SS): S119, 1999.

Bussemakers MJ. van Moorselaar RJ. Giroldi LA. Ichikawa T. Isaacs JT. Takeichi M. Debruyne FM. Schalken JA. Decreased expression of E–cadherin in the progression of rat prostatic cancer. Cancer Research 52(10):2916–22, 1992.

Catalona WJ. Partin AW. Slawin KM. Brawer MK. Flanigan RC. Patel A. Richie JP. deKernion JB. Walsh PC. Scardino PT. Lange PH. Subong EN. Parson RE. Gasior GH. Loveland KG. Southwick PC. Use of the percentage of free prostate–specific antigen to enhance differentiation of prostate cancer from benign prostatic disease: a prospective multicenter clinical trial [see comments]. JAMA. 279(19):1542–7, 1998.

Dong JT. Lamb PW. Rinker–Schaeffer CW. Vukanovic J. Ichikawa T. Isaacs JT. Barret JC. KAI1, a metastasis suppressor gene for prostate cancer on human chromosome 11p11.2 [see comments]. Science. 268(5212):884–6, 1995.

Dong JT. Suzuki H. Pin SS. Bova GS. Schalken JA. Isaacs WB. Barrett JC. Isaacs JT. Down–regulation of the KAI1 metastasis suppressor gene during the progression of human prostatic cancer infrequently involves gene mutation or allelic loss. Cancer Research. 56(19):4387–90, 1996.

Dunn JE. Cancer epidemiology in populations of the United States—with emphasis on Hawaii and California—and Japan. Cancer Research. 35(11 Pt. 2):3240–5. 1975.

Fornaro M. Tallini G. Bofetiado CJ. Bosari S. Languino LR. Down–regulation of beta 1C integrin, an inhibitor of cell proliferation, in prostate carcinoma. American Journal of Pathology. 149(3):765–73. 1996.

Fornaro M. Manzotti M. Tallini G. Slear AE. Bosari S. Ruoslahti E. Languino LR. Beta1C integrin in epithelial cells correlates with a nonproliferative phenotype: forced expression of beta1C inhibits prostate epithelial cell proliferation. American Journal of Pathology. 153(4):1079–87, 1998.

(List continued on next page.)

*Primary Examiner*—James Housel
*Assistant Examiner*—Zachariah Lucas
(74) *Attorney, Agent, or Firm*—Brian S. Steinberger; Law Offices of Brian S. Steinberger, P.A.; Frances L. Olmsted

(57) ABSTRACT

Prostasin protein has been found to be a useful marker for determination of the invasiveness of and as a means to treat human carcinomas. Using RT-PCR and western blot analyses, prostasin protein and mRNA expression were found in normal human prostate epithelial cells and the human prostate cancer cell line LNCaP, but not in the highly invasive human prostate cancer cell lines DU-145 and PC-3. Imunohistochemistry studies of human prostate cancer specimens revealed a down-regulation of prostasin in high-grade tumors. Using RT-PCR and western blot analyses, prostasin protein and mRNA expression were found in a non-invasive human breast cancer cell line, MCF-7, while invasive human breast cancer cell lines MDA-MB-231 and MDA-MB-435s were found not to express either the prostasin protein or the mRNA. A non-invasive human breast cancer cell line, MDA-MB-453, was shown to express prostasin mRNA but not prostasin protein. Transfection of DU-145 and PC-3 cells with a full-length human prostasin cDNA restored prostasin expression and reduced the in vitro invasiveness by 68% and 42%, respectively. Transfection of MDA-MB-231 and MDA-MB-435s cells with a full-length human prostasin cDNA restored prostasin expression and reduced the in vitro invasiveness by 50% for either cell line.

6 Claims, 7 Drawing Sheets

OTHER PUBLICATIONS

Fornaro M. Tallini G. Zheng DQ. Flanagan WM. Manzotti M. Languino LR. p27(kip1) acts as a downstream effector of and is coexpressed with the beta1C integrin in prostatic adenocarcinoma. Journal of Clinical Investigation. 103(3):321–9, 1999.

Gao AC. Lou W. Dong JT. Isaacs JT. CD44 is a metastasis suppressor gene for prostatic cancer located on human chromosome 11p13. Cancer Research. 57(5):846–9, 1997.

Goyal J. Smith KM. Cowan JM. Wazer DE. Lee SW. Band V. The role for NES1 serine protease as a novel tumor suppressor. Cancer Res 58:4782–4786, 1998.

Greene GF. Kitadai Y. Pettaway CA. von Eschenbach AC. Bucana CD. Fidler IJ. Correlation of metastasis–related gene expression with metastatic potential in human prostate carcinoma cells implanted in nude mice using an in situ messenger RNA hybridization technique. American Journal of Pathology. 150(5):1571–82, 1997.

Greenlee RT. Murray T. Bolden S. Wingo PA. Cancer statistics. 1999. Ca: a Cancer Journal for Clinicians 2000;50:7–33.

Hooper JD. Nicol DL. Dickinson JL. Eyre HJ. Scarman AL. Normyle JF. Stuttgen MA. Douglas ML. Loveland KA. Sutherland GR. Antalis TM. Testisin, a new human serine proteinase expressed by premeiotic testicular germ cells and lost in testicular germ cell tumors. Cancer Research. 59(13):3199–205, 1999.

Isaacs JT. Molecular markers for prostate cancer metastasis. Developing diagnostic methods for predicting the aggressiveness of prostate cancer. [Review] [92 refs] American Journal of Pathology. 150(5):1511–21, 1997.

Isaacs JT. Bova GS. Prostate Cancer. In *The Genetic Basis of Human Cancer* (Eds. Vogelstein B and Kinzler KW). pp653–60, McGraw–Hill Health Professions Division. 1998.

Knuutila S. Aalto Y. Autio K. Bjorkqvist AM. El–Rifai W. Hemmer S. Huhta T. Kettunen E. Kiuru–Kuhlefelt S. Larramendy ML. Lushnikova T. Monni O. Pere H. Tapper J. Tarkkanen M. Varis A. Wasenius VM. Wolf M. Zhu Y. DNA copy number losses in human neoplasms. [Review] [197 refs] American Journal of Pathology. 155(3):683–94. 1999.

Liu DF. Rabbani SA. Induction of urinary plasminogen activator by retinoic acid results in increased invasiveness of human prostate cancer cells PC–3. Prostate. 27(5):269–76. 1995.

Lou W. Krill D. Dhir R. Becich MJ. Dong JT. Frierson HF Jr. Isaacs WB. Isaacs JT. Gao AC. Methylation of the CD44 metastasis suppressor gene in human prostate cancer. Cancer Research. 59(10):2329–31, 1999.

Lou J. Lubaroff DM. Hendrix MJ. Suppression of prostate cancer invasive potential and matrix metalloproteinase activity by E–cadherin transfection. Cancer Research. 59(15):3552–6, 1999.

Mirchandani D. Zheng J. Miller GJ. Ghosh AK. Shibata DK. Cote RJ. Roy–Burman P. Heterogeneity in intratumor distribution of p53 mutations in human prostate cancer. American Journal of Pathology. 147(1):92–101, 1995.

Nelson PS. Gan L. Ferguson C. Moss P. Gelinas R. Hood L. Wang K. Molecular cloning and characterization of prostase, an androgen–regulated serine protease with prostate–restricted expression. Proceedings of the National Academy of Sciences of the United States of America. 96(6):3114–9, 1999.

Noordzij MA. van Steenbrugge GJ. Verkaik NS. Schroder FH. van der Kwast TH. The prognostic value of CD44 isoforms in prostate cancer patients treated by radical prostatectomy. Clinical Cancer Research. 3(5):805–15, 1997.

Qian J. Bostwick DG. Takahashi S. Borell TJ. Herath JF. Lieber MM. Jenkins RB. Chromosomal anomalies in prostatic intraepithelial neoplasia and carcinoma detected by fluorescence in situ hybridization. Cancer Research. 55(22):5408–14, 1995.

Saedi MS. Hill Tm. Kuus–Reichel K. Kumar A. Payne J. Mikolajczyk SD. Wolfert RL. Rittenhouse HG. The precursor form of the human kallikrein 2. a kallikrein homologous to prostate–specific antigen, is present in human sera and is increased in prostate cancer and benign prostatic hyperplasia. Clinical Chemistry. 44(10):2115–9, 1998.

Sakr WA. Macoska JA. Benson P. Grignon DJ. Wolman SR. Pontes JE. Crissman JD. Allelic loss in locally metastatic, multisampled prostate cancer. Cancer Research. 54(12):3273–7, 1994.

Stamey TA, McNeal JE. Yemoto CM. Sigal BM, Johnstone IM. Biological determinants of cancer progression in men with prostate cancer. JAMA 281:1395–1400. 1999.

Tsihlias J. Kapusta LR. DeBoer G. Morava–Protzner I. Zbieranowski I. Bhattacharya N. Catzavelos GC. Klotz LH. Slingerland JM. Loss of cyclin–dependent kinase inhibitor p27Kip1 is a novel prognostic factor in localized human prostate adenocarcinoma. Cancer Research. 58(3):542–8, 1998.

Ueda T. Ichikawa, T. Tamaru J. Mikata A. Akakura K. Akimoto S. Imai T. Yoshie O. Shiraishi T. Yatani R. Ito H. Shimazaki J. Expression of the KAI1 protein in benign prostatic hyperplasia and prostate cancer. American Journal of Pathology. 149(5):1435–40, 1996.

Umbas R. Schalken JA. Aalders TW. Carter BS. Karthaus HF. Schaafsma HE. Debruyne FM. Isaacs WB. Expression of the cellular adhesion molecule E–cadherin is reduced or absent in high–grade prostate cancer. Cancer Research. 52(18):5104–9, 1992.

Umbas R. Isaacs WB. Bringuier PP. Schaafsma HE. Karthaus HF. Oosterhof GO. Debruyne FM. Schalken JA. Decreased E–cadherin expression is associated with poor prognosis in patients with prostate cancer. Cancer Research. 54(14):3929–33, 1994.

Vallet V. Chraibi A. Gaeggeler HP. Horisberger JD. Rossier BC. An epithelial serine protease activates the amiloride–sensitive sodium channel. Nature. 389(6651):607–10, 1997.

Yu JX. Chao L. Chao J. Prostasin is a novel human serine proteinase from seminal fluid. Purification, tissue distribution, and localization in prostate gland. Journal of Biological Chemistry. 269(29):18843–8. 1994.

Yu JX. Chao L. Chao J. Molecular cloning, tissue–specific expression, and cellular localization of human prostasin mRNA, Journal of Biological Chemistry, 270(22):13483–9, 1995.

Yu JX. Chao L. Ward DC. Chao J. Structure and chromosomal localization of the human prostasin (PRSS8) gene. Genomics. 32(3):334–40, 1996.

Zaugg K. Bodis S. Is there a role for molecular prognostic factors in the clinical management of ductal carcinoma in situ (DCIS) of the breast?. [Review] [49 refs] Radiotherapy & Oncology. 55(2):95–9, 2000.

Emmert–Buck, et al., Laser Capture Microdissection *Science*, vol. 274, Nov. 8, 1997, pp. 998–1001.

* cited by examiner

METHOD OF IDENTIFYING AND TREATING INVASIVE CARCINOMAS

This invention relates to prostasin and its use in the diagnosis and treatment of prostate and breast cancers, and is a divisional application to U.S. application Ser. No. 09/755,811 filed on Jan. 5, 2001, now U.S. Pat. No. 6,569,684, which claims the priority to U.S. Provisional Application Ser. No. 60/174,801 filed Jan. 6, 2000 and was supported in part by Department of Defense Prostate Cancer Research Grant DAMD17-98-1-8590, and in part by grants to principal investigator K. X. CHAI from the Florida Hospital Gala Endowed Program for Oncologic Research.

BACKGROUND AND PRIOR ART

For men in the U.S., prostate cancer is the most commonly diagnosed cancer, and the second leading cause of cancer-related death (Greenlee R T, Murray T, Bolden S, Wingo P A. Cancer statistics, 1999. Ca: a Cancer Journal for Clinicians 2000:50:7–33). Prostate cancers originate as localized lesions; some of these localized lesions will progress to become invasive, migratory and metastatic. Our current understanding of the mechanisms of the prostate cancer invasion process, however, is poor. Our ability to predict the acquisition of invasive potentials by a prostate cancer is limited.

The mechanisms leading to the development of a prostate cancer are complex. Currently, it is believed to be the result of multiple transformation steps from normal prostate glandular cells (Carter H B, Piantadosi S, Isaacs J T. Clinical evidence for and implications of the multistep development of prostate cancer. Journal of Urology, 143(4):742–6, 1990). The initial steps result in what are described as prostatic interepithelial neoplastic (PIN) lesions (Isaacs J T, Molecular markers for prostate cancer metastasis. Developing diagnostic methods for predicting the aggressiveness of prostate cancer. [Review] [92 refs] American Journal of Pathology, 150(5):1511–21, 1997). These PIN lesions may then typically have three different fates based on an assessment of their impact to the patient. The PIN lesions can remain as such, not producing histologically detectable prostate cancer, or further transform into histologically detectable prostate cancer. Most of the histologically detectable prostate cancers will be asymtomatic in the patient and remain non-manifest clinically as many are discovered post-mortem (Carter H Coffey D, Prostate Cancer: the magnitude of the problem in the United States. In a Multidisciplinary Analysis of Controversies in the Management of Prostate Cancer. (Eds. Coffey D, Resnick M, Door R, et al.), pp 1–9, Plenum Press a 1988; Carter H B Piantadosi S, Issacs J T, Clinical evidence for implications of the multistep development of prostate cancer, Journal of Urology, 143(4):742–6, 1990; Scardino P T, Weaver R, Hudson M A. Early detection of prostate cancer. [Review] [102 refs] Human Pathology, 23(3):211–22, 1999). Prostate cancers are diagnosed clinically by an estimate of size and location using the TNM staging system (Denis L J, Staging and prognosis of prostate cancer. European Urology, 24 Suppl 2:13–8, 1993), and by pathological staging based on an examination of the histology of the removed prostate via either biopsy or prostatectomy using a system by D. F. Gleason, (Gleason D F, Classification of prostatic carcinomas. Cancer Chemotherapy Reports-Part 1, 50(3):125–8, 1966). About 50% of prostate cancer cases receiving treatment are diagnosed clinically as advanced, or, non-organ-confined (Scardino P T, Weaver R, Hudson M A. Early detection of prostate cancer. [Review] [102 refs] Human Pathology, 23(3):211–22, 1992), for which no effective treatment exists (Yagoda A, Petrylak D. Cytotoxic chemotherapy for advanced hormone-resistant prostate cancer, [Review] [63 refs] Cancer. 71(3 Suppl): 1098–109, 1993 and Petrylak, 1993). Of the remaining 50% cases, ⅓ (~50,000) are diagnosed as organ-confined but micrometastasis may be present. The final group of patients (~100,000) have truly organ-confined prostate cancer and can be cured by radical prostatectomy (Sgrignoli A R Walsh P C, Steinberg G D, Steiner M S, Epstein J I. Prognostic factors in men with stage D 1 prostate cancer: identification of patients less likely to have prolonged survival after radical prostatectomy [see comments]. Journal of Urology, 152(4):1077–81, 1994; Zincke H, Oesterling J E, Blute N L, Bergstralh E J, Myers R P, Barrett D M, long term (15 years) results after radical prostatectomy for clinically localized (stage T2c or lower) prostate cancer [see comments]. Journal of Urology, 152(5 Pt 2): 1850–7, 1994) or left untreated (watchful waiting) without the risk of life-threatening or life-altering. For the patients with non-organ-confined prostate cancers (discovered via either biopsy or surgery), undergoing systemic treatment early is essential to the management of their cancer (Yagoda A, Petrylak D. Cytotixic chemotherapy for advanced hormone-resistant prostate cancer [Review] [63 refs] Cancer, 71(3 Suppl): 1098–109, 1993). Consequently, it will be ideal, both medically and economically, if one could precisely predict upon early pathological examination of the tumor, which group of patients will have truly organ-confined disease versus which group will have invasive prostate cancer.

Clinical staging of prostate cancer generally depends on the results of three tests that are performed in the following order: a PSA (prostate-specific antigen) blood test as a screening method; DRE (digital rectal examination) for an initial indication of palpable disease; and, a biopsy to obtain samples for histological examination. Prostate cancers, removed either via biopsy or surgery, are graded histologically by the system of Gleason. (Gleason D F, Classification of prostatic carcinomas. Cancer Chemotherapy Reports—Part 1, 50(3):125–8, 1966), which is an evaluation of how aggressive and how poorly-differentiated the prostate cancers are. The aggressiveness of prostate tumors: of low Gleason scores (<5) is limited; of high Gleason scores (8–10) are highly aggressive; but, for the intermediate Gleason-score (5–7) prostate cancers (76% of prostate tumors), the accuracy of predicting their aggressiveness is poor (Gleason D F, Mellinger G T. Prediction of prognosis for prostatic adenocarcinoma by combined histological grading and clinical staging, Journal of Urology, 111(1): 58–64, 1974). Thus, the ability to accurately determine the aggressiveness of these intermediate Gleason-score prostate tumors has remained as a practical challenge to, and a primary goal for, prostate cancer research (Isaacs J T, Molecular markers for prostate cancer metastasis. Developing diagnostic methods for predicting the aggressiveness of prostate cancer. [Review] [92 refs] American Journal of Pathology, 150(5):1511–21, 1997). Especially with regard to the number of patients (150,000) facing a decision of whether to undergo systemic treatment, the most urgent demand in prostate cancer care is the development of methods to enhance our ability to accurately predict the aggressiveness of the tumors with Gleason scores of 5–7.

It is now commonly believed that cancers occur via multiple transformation steps by accumulating mutations in three classes of genes: proto-oncogenes (Park M, Oncogenes. In The Genetic Basis of Human Cancer (Eds. Vogelstein B and Kinzler K W), pp205–28. McGraw-Hill Health Professions Divisions, 1998); tumor-suppressor genes (Knuutila S, Aalto Y, Bjorkqvist A M, EL-Rifai W, Hemmer S, Huhta T, Kettunen E, Kiuru-Kuhlefelt S, Larramendy M L, Lushnikova T, Monni O, Pere H, Tapper J, Tarkkanen M, Varis A, Wasenius V M, Wolf M, Zhu Y, DNA copy number losses in human neoplasms. [Review] [197 refs] American Journal of Pathology, 155(3):683–94, 1999); and, DNA repair genes (Knuutila S, Aslto Y, Bjorkqvit A M, EL-Rifai W, Hemmer S, Huhta T, Kettunen E, Kiuru-Kuhlefelt S, Larramedy M L, Lushnikova T, Monni O, Pere H, Tapper J, Tarkkanen M, Varis A, Wasenius V M, Wolf M, Zhu Y. DNA copy number losses in human neoplasms. [Review] [197 refs] American Journal of Pathology, 155(3):683–94, 1999). The histological prostate cancers for which the prediction of clinical aggressiveness is difficult (those with the intermediate Gleason scores 5–7) probably have not gone through the necessary "multi-step" transformation to acquire the potentials to behave aggressively (as would the high-grade cancers). This notion was supported by studies comparing the course of prostate cancer development among men in Japan and in the U.S., and Japanese men who migrated to the U.S. (Carter H B, Piantadosi S, Isaacs J T. Clinical evidence for and implications of the multistep development of prostate cancer. Journal of Urology, 1990; Haenszel W, Kurihara M, Studies of Japanese Migrants, I. Mortality form cancer and other diseases among Japanese in the United States. Journal of the National Cancer Institute,40(1):43–68, 1968: Akazaki K, Stemmerman G N. Comparative study of latent carcinoma of the prostate among Japanese in Japan and Hawaii. Journal of the National Cancer Institute. 50(5): 1137–44, 1973; Dunn J E, Cancer epidemiology in populations of the United States—with emphasis on Hawaii and California—and Japan. Cancer Research, 35( 11 Pt.2): 3240–5, 1975). The findings were that first- and second-generation Japanese men who migrated to the U.S. have a higher prostate cancer incident rate than native Japanese men. The emigrant Japanese men's prostate cancer incident rate is similar to that of men in the U.S. Investigating the changes of expression in these three classes of cancer-relevant genes during the course of prostate cancer development will lead to a better understanding of the processes by which prostate cancers acquire their aggressive potentials. The discovery of molecules whose changes can be correlated to the staging of prostate cancer will provide new tools to improve our ability to better predict the aggressive behaviors of prostate cancer. This approach is now commonly referred to as "molecular staging".

Down-regulated genes such as tumor suppressors, invasion suppressors or metastasis suppressors may be used as prostate cancer markers. Examples of these genes that can potentially serve as prostate cancer markers for "molecular staging" are: KAI1 (Dong J T, Suzuki H, Pin S S, Bova G S., Schalken J A, Issacs W B, Barrett J C, Issace I T, Down-regulation of the KA11 metastasis suppressor gene during the progression of human prostatic cancer infrequently involves gene mutation or allelic loss. Cancer Research, 56(19): 4387–90, 1996); (Ueda T, Ichikawa T., Tamaru j, Mikata A, Akakura K, Akimoto S, Imai T, Yoshie O, Shiraishi T, Yatani R, Ito H, Shimazaki J., Expression fof the KA11 protein in benign prostatic hyperplasia and prostate cancer. American Journal of Pathology 149(5): 1435–40, 1996): E-cadherin (Umbas R, Isaacs W B Bringuier P P, Schaafsma H E, Karthaus H F, Oosterhof G O, Debruyne F M, Schalken J A, Decreased E-Cadherin expression is associated with poor prognosis is patients with prostate cancer. Cancer Research, 52(18):5104–9, 1992, Umbas R, Isaacs W B, Bringuier P P, Schaafsma H E, Karthaus H F, Oosterhof G O Debruyne F M, Schalken J A, Decreased E-cadherin expression is associated with poor prognosis in patients with prostate cancer. Cancer Research, 54(14):3929–33, 1994); $\beta_{1C}$ integrin (Fornaro M, Tallini G, Bofetiado C J, Bosari S, Languino L R. Down-regulation of $\beta_{1C}$ integrin, an inhibitor of cell proliferation, in prostate carcinoma. American Journal of Pathology, 149(3):765–73, 1996Fornaro M, Manzotti M, Tallini G, Slear A E, Bosari S, Ruoslahti E, Languino L R. β1C integrin in epithelial cells correlates with a nonproliferative phenotype: forced expression of β1C inhibits prostate epithelial cell proliferation. American Journal of Pathology. 153(4):1079–87, 1998; p27 (kip1) (Tsihlias J, Kapusta L R, DeBoer G, Morava-Protzner I, Zbieranowski I, Bhattacharya N, Catzavelos G C, Klotz L H, Slingerland J M, Loss of cyclin-dependent kinase inhibitor p27Kip1 is a novel prognostic factor in localized human prostate adenocarcinoma. Cancer Research, 58(3):542–8, 1998); and CD44 (Lou W, Krill D, Dhir R, Becich M J, Dong J T, Frierson H F Jr. Isaacs W B, Isaacs J T, Gao A C. Methylation of the CD44 metastasis suppressor gene in human prostate cancer. Cancer Research, 59(10):2329–31, 1999). By using the method of immunohistochemistry, these genes were found to be down-regulated in prostate cancer. KAI's down regulation is a potential predictor of metastasis (Dong, et al., 1996: Ueda et al., 1996). While E-cadherin's down regulation is strongly correlated to higher Gleason grades. Functional studies of these genes have given clues to their role in prostate cancer or normal prostate biology. (Debruyne F M, Isaacs W B, Expression of the cellular adhesion molecule E-cadherin is reduced or absent in high-grade prostate cancer. Cancer Research, 52(18):5104–9, 1992; Umbas R, Isaacs W B, Bringuier P P, Schaafsma H E, Karthaus H F, Oosterhof G O Debruyne F M, Schalken J A. Decreased E-cadherin expression is associated with poor prognosis in patients with prostate cancer. Cancer Research, 54(14):3929–33, 1994; metastasis suppressor gene during the progression of human prostatic cancer infrequently involves gene mutation or allelic loss. Cancer Research, 56(19):4387–90; 1996 Ueda T, Ichikawa T, Tamaru J, Mikata A, Akakura K, Akimoto S, Imai T, Yoshie O, Shiraishi T, Yatani R, Ito H, Shimazaki J. Expression of the KAI1 protein in benign prostatic hyperplasia and prostate cancer. American Journal of Pathology, 149(5):1435–40, 1996) while E-cadherin's down-regulation is strongly correlated to higher Gleason grades (Umbas R, Schalken J A, Aalders T W, Carter B S, Karthaus H F, Schaafsma H E, Debruyne F M, Isaacs W B. Expression of the cellular adhesion molecule E-cadherin is reduced or absent in high-grade prostate cancer. Cancer Research, 52(18):5104–9, 1992; Umbas R, Isaacs W B, Bringuier P P, Schaafsma H E, Karthaus H F, Oosterhof G O, Debruyne F M, Schalken J A. Decreased E-cadherin expression is associated with poor prognosis in patients with prostate cancer. Cancer Research, 54(14):3929–33, 1994) Functional studies of these genes have given clues to their role in prostate cancer or normal prostate biology. Human KAI suppress metastasis of rat prostate cancer cells upon gene transfer (Dong J T, Lamb P W, Rinker-Schaeffer C W, Vukanovic J, Ichikawa T, Isaacs J T, Barrett J C. KAI1, a metastasis suppressor gene for prostate cancer on human chromosome 11p11.2 [see comments]. Science, 268(5212):884–6, 1995). $\beta_{1C}$ and p27 (kip1) are involved in signaling pathway that inhibits cell proliferation (Fornaro M, Tallini G, Zheng D Q, Flanagan W M, Manzotti M, Languino L R, p27(kip1) acts as a downstream effector of and is coexpressed with the beta1C integrin in prostatic adenocarcinoma. Journal of Clinical Investigation, 103(3):321–9, 1999). E-cadherin expression is progressively lost during the transformation of rat prostate cancer from non-invasive to invasive (Bussemakers M J, van Moorselaar R J, Giroldi L A, Ichikawa T, Isaacs J T, Takeichi M, Debruyne F M, Schalken J A. Decreased expression of E-cadherin in the progression of rat prostatic cancer. Cancer Research, 52(10):2916–22, 1992), and it has also been shown to be an invasion suppressor (Lou W, Krill D, Dhir R, Becich M J, Dong J T, Frierson H F Jr. Isaacs W B, Isaacs J T, Gao A C. Methylation of the CD44 metastasis suppressor gene in human prostate cancer. Cancer Research, 59(10):2329–31, 1999). CD44 loss of expression is associated with high metastatic ability and transfection of CD44 suppresses metastasis without affecting tumorigenecity of rat prostate cancer cells (Gao A C, Lou W, Dong J T, Isaacs J T. CD44 is a metastasis suppressor gene for prostatic cancer located on human chromosome 11p13. Cancer Research, 57(5):846–9, 1997). CD44 down-regulation is a prognostic marker for prostate cancer (Noordzij M A, van Steenbrugge G J, Verkaik N S, Schroder F H, van der Kvast T H. The prognostic value of CD44 isoforms in prostate cancer patients treated by radical prostatectomy. Clinical Cancer Research, 3(5):805–15, 1997).

Human prostate cancer histology is heterogeneous, or "multi-focal" in nature (Isaacs J T, Bova G S, Prostate Cancer. In *The Genetic Basis of Human Cancer* (Eds. Vogelstein B and Kinzler K W), pp653–60, McGraw-Hill Health Professions Division, 1998 and Bova, 1998), with an average of five lesions in a patient (Bastacky S I, Wojno K J, Walsh P C, Carmichael M J, Epstein J I. Pathological features of hereditary prostate cancer. Journal of Urology, 153(3 Pt 2):987–92, 1995). Between the tumor regions of a prostate and within a single tumor region, the genetic causes to the cancer are heterogeneous and independent as well (Sakr W A, Macoska J A, Benson P, Grignon D J, Wolman S R, Pontes J E, Crissman J D. Allelic loss in locally metastatic, multisampled prostate cancer. Cancer Research, 54(12):3273–7, 1994; Qian J, Bostwick D G, Takahashi S, Borell T J, Herath J F, Lieber M M, Jenkins R B. Chromosomal anomalies in prostatic intraepithelial neoplasia and carcinoma detected by fluorescence in situ hybridization. Cancer Research, 55(22):5408–14, 1995; Mirchandani D, Zheng J, Miller G J, Ghosh A K, Shibata D K, Cote R J, Roy-Burman P. Heterogeneity in intratumor distribution of p53 mutations in human prostate cancer. American Journal of Pathology, 147(1):92–101, 1995). In the end, the best predictor of prostate cancer's potential to gain invasiveness may be a consideration of a number of genes whose expression levels change along the course of cancer development, as demonstrated in principle by Greene et al. (Greene G F, Kitadai Y, Pettaway C A, von Eschenbach A C, Buucana C D, Fidler I J. Correlation of metastasis-related gene expression with metastatic potential in human prostate carcinoma cells implanted in nude mice using an in situ messenger RNA hybridization technique. American Journal of Pathology, 150(5):1571–82, 1997). Hence, expanding the repertoire of such genes, including both the onco-genes and the suppressor genes, will enhance the accuracy and dependability of this approach.

As for the treatment options of prostate cancer, patients with truly organ-confined prostate cancer can be cured by radical prostatectomy. Patients with non-organ-confined prostate cancers, however, have very low survival rates and the current treatments are largely ineffective (Yagoda A, Petrylak D, Cytotoxic chemotherapy for advanced hormone-resistant prostate cancer. [Review] [63 refs] Cancer, 71(3 Suppl):1098–109, 1993).

Breast cancer is the most diagnosed cancer in women and the second leading cancer related cause of death in women (Greenlee R T, Murray T, Bolden S, Wingo P A, Cancer statistics, 1999, Ca: a Cancer Journal for Clinicians 2000;50:7–33). Breast ductal carcinoma in situ (hereinafter indicated as DCIS) incidence has increased dramatically since 1983 as a result of implementing screening programs (Ernster V L, Barclay J. Increases in ductal carcinoma in situ (DCIS) of the breast in relation to mammography: a dilemma. [Review] [34 refs] Journal of the National Cancer Institute. Monographs, (22):151–6, 1997). DCIS is described as a malignant growth of epithelial cells within the ducts and lobules of the breast, and is believed to be the precursor of all invasive breast carcinoma. DCIS itself is non-life-threatening; however, current treatment options for DCIS include masectomy, lumpectomy, radiotherapy or tamoxifen (Ernster V L, Barclay J. Increases in ductal carcinoma in situ (DCIS) of the breast in relation to mammography: a dilemma. [Review] [34 refs] Journal of the National Cancer Institute. Monographs, (22):151–6, 1997; Hwang E S, Esserman L J. Management of ductal carcinoma in situ, [Review] [91 refs] Surgical Clinics of North America. 79(5):1007–30, viii, 1999). These treatment options for DCIS are at best controversial due primarily to a lack of precision in diagnosis and prognosis of whether the detected DCIS will progress to invasive breast cancer and whether recurrence is likely after treatment, usually with a high percentage being invasive breast cancer (Zaugg K, Bodis S. Is there a role for molecular prognostic factors in the clinical management of ductal carcinoma in situ (DCIS) of the breast [Review] [49 refs] Radiotherapy & Oncology, 55(2):95–9, 2000). At present, histological grading (nuclear grading and whether come do-type necrosis is present) and the size of the DCIS are used to provide assessments of risk of DCIS to progress into invasive breast cancer (Zaugg K, Bodis S. Is there a role for molecular prognostic factors in the clinical management of ductal carcinoma in situ (DCIS) of the breast?. [Review] [49 refs] Radiotherapy & Oncology, 55(2):95–9, 2000; Shoker B S, Sloane J P, DCIS grading schemes and clinical implications. [Review] [40 refs] Histopathology, 35(5):393–400, 19; van de Vijver M J. Ductal carcinoma in situ of the breast: histological classification and genetic alterations. [Review] [69 refs] Recent Results in Cancer Research, 152:123–34, 1998). These parameters are far from being adequate for making the most accurate choice of treatment, resulting in a choice either overly excessive or conservative, in either case, the patient will suffer unnecessarily. Molecular markers can help improve our ability to better diagnose DCIS and stratify treatment options, especially the molecular markers that, themselves, play a role in the progression of DCIS to invasive breast cancer (Zaugg K, Bodis S. Is there a role for molecular prognostic factors in the clinical management of ductal carcinoma in situ (DCIS) of the breast?. [Review][49 refs] Radiotherapy & Oncology, 55(2):95–9, 2000; Silverstein M J, Masetti R. Hypothesis and practice; are there several types of treatment for ductal carcinoma in situ of the breast?. [Review] [53 refs] Recent Results in Cancer Research, 152:105–22, 1998). The tumorigenesis process is a multi-step transformation in which molecular events escalate to the final stage of invasive phenotype (Silverstein M J, Masetti R. Hypothesis and practice: are there several types of treatment for ductal carcinoma in situ of the breast?. [Review] [53 refs] Recent Results in Cancer Research, 152:105–22, 1998). The conventional paradigm of protease involvement in the development and progression of cancer has been the assignment of a usually negative role to the proteases, such as promoting tumor invasion (Mignatti P, Rifkin D B, Biology and biochemistry of proteinases in tumor invasion. [Review] [306 refs] Physiological Reviews, 73(1):161–95, 1993). In turn, the conventional paradigm of protease inhibitors in relation to cancer is usually regard of a beneficial effect for the presence of these molecules (Kennedy A R. Chemopreventive agents: protease inhibitors. Pharmacol Therapeut 78:167–209, 1998). Recently, however, the picture of a new paradigm is beginning to emerge for several serine proteases in breast, prostate, and testicular cancers. A "normal epithelial cell specific-1" (NES 1) serine protease was found to be down-regulated in breast and prostate cancers, and it functions as a tumor suppressor (Goyal J, Smith K M, Cowan J M, Wazer D E, Lee S W, Band V. The role for NES1 serine protease as a novel tumor suppressor. Cancer Res 58:4782–4786, 1998). A prostate-specific serine protease, prostase (Nelson P S, Gan L, Ferguson C, Moss P, Gelinas R, Hood L, Wang K. Molecular cloning and characterization of prostase, an androgen-regulated serine protease with prostate-restricted expression. Proceedings of the National Academy of Sciences of the United States of America, 96(6):3114–9, 1999), was shown to be expressed in normal prostate but not in prostate cancer cell lines DU-145 and PC-3. The expression of a testis-specific serine protease, testisin, was shown to be lost in testicular cancer through either a loss of gene (Hooper J D, Nicol D L, Dickinson J L, Eyre H J, Scarman A L, Normyle J F, Stuttgen M A, Douglas M L, Loveland K A, Sutherland G R, Antalis T I. Testisin, a new human serine proteinase expressed by premeiotic testicular germ cells and lost in testicular germ cell tumors. Cancer Research, 59(13): 3199–205, 1999) or methylation in the promoter (Boucaut K, Douglas M, Clements J, Antalis T. The serine proteinase testisin may act as a tumor and/or growth suppressor in the testis and may be regulated by DNA methylation. Cancer Genetics and Tumor Suppressor Genes, Cold Spring Harbor Laboratory, 2000). Further, transfection of human testicular cancer cells with a testisin cDNA reduced the tumor growth of xenografts of these cells in nude mice, suggesting a tumor suppressor function for testisin (Boucaut K, Douglas M, Clements J, Antalis T. The serine proteinase testisin may act as a tumor and/or growth suppressor in the testis and may be regulated by DNA methylation. Cancer Genetics and Tumor Suppressor Genes, Cold Spring Harbor Laboratory, 2000). The testisin serine protease is potentially membrane-bound as suggested by its structure and confirmed by immunohistochemistry gene (Hooper J D, Nicol D L, Dickinson J L, Eyre H J, Scarman A L, Normyle J F, Stuttgen M A, Douglas M L, Loveland K A, Sutherland G R, Antalis T M. Testisin, a new human serine proteinase expressed by premeiotic testicular germ cells and lost in testicular germ cell rumors. Cancer Research, 59(13):3199–205, 1999.) Prostasin serine protease is an acidic protein (p1 4.5–4.8) of approximately 40 kDa in molecular mass (Yu J X, Chao L, Chao J, Prostasin is a novel human serine proteinase from seminal fluid. Purification, tissue distribution, and localization in prostate gland. Journal of Biological Chemistry. 269(29): 18843–8, 1994), it is predominantly made in the prostate gland (~140 ng/mg protein), with lesser amounts (2–6 ng/mg protein) also found in the bronchi, colon, kidney, liver, lung, pancreas, and the salivary glands (Yu J X, Chao L, Chao J. Prostasin is a novel human serine proteinase from seminal fluid. Purification, tissue distribution, and localization in prostate gland. Journal of Biological Chemistry, 269(29): 18843–8, 1994). Prostasin is secreted in the prostatic fluid, and can be detected in the semen (~9 µg/ml). Prostasin expression is localized to the epithelial cells of human prostate gland by in situ hybridization histochemistry using an antibody or an anti-sense RNA probe (Yu J X, Chao L, Chao J. Prostasin is a novel human serine proteinase from seminal fluid. Purification, tissue distribution, and localization in prostate gland. Journal of Biological Chemistry, 269(29):18843–8, 1994; (Yu J X, Chao L, Chao J. Molecular cloning, tissue-specific expression, and cellular localization of human prostasin mRNA. Journal of Biological Chemistry, 270(22):13483–9, 1995). Molecular cloning of a full-length human prostasin cDNA revealed that its predicted amino acid residue sequence contains a carboxyl-terminal hydrophobic region that can potentially anchor the protein on the membrane (Yu J X Chao L, Chao J. Molecular cloning, tissue-specific expression, and cellular localization of human prostasin mRNA. Journal of Biological Chemistry, 270(22):13483–9, 1995). At the amino acid level, prostasin is similar to plasma kallikrein, coagulation factor XI, hepsin, plasminogen, acrosin, prostase, and, in particular, testisin (sharing 44% sequence identity) [Nelson P S, Gan L, Feruuson C, Moss P, Gelinas R, Hood L, Wang K. Molecular cloning and characterization of prostase, an androgen-regulated serine protease with prostate-restricted expression, Proceedings of the National Academy of Sciences of the United States of America, 96(6):3114–9, 1999; Hooper J D, Nicol D L, Dickinson J L, Eyre H J, Scarman A L, Normyle J F, Stuttgen M A, Douglas M L, Loveland K A, Sutherland G R, Antalis T M. Testisin, a new human serine proteinase expressed by premeiotic testicular germ cells and lost in testicular germ cell tumors. Cancer Research, 59(13): 3199–205, 1999; Yu J X, Chao L, Chao J. Molecular cloning, tissue-specific expression, and cellular localization of human prostasin mRNA. Journal of Biological Chemistry, 270(22): 13483–9, 1995). A membrane-bound Xenopus kidney epithelial cell sodium channel-activating protease (CAP1) was shown to be highly homologous to human prostasin as well (sharing 53% sequence identity at the amino acid level) (Vallet V, Chraibi A, Gaeggeler H P, Horisberger J D, Rossier B C. An epithelial serine protease activates the amiloride-sensitive sodium channel. Nature, 389(6651):607–10, 1997). Prostasin is encoded by a single-copied gene, which is located on human chromosome 16p11.2 (Yu J X, Chao L, Ward D C, Chao J. Structure and chromosomal localization of the human prostasin (PRSS8) gene. Genomics, 32(3):334–40, 1996). The secreted prostasin cleaves synthetic substrates in vitro preferentially at the carboxyl-terminal side of Arg residue, and is thus considered a trypsin-like serine protease (Yu J X, Chao L, Chao J. Prostasin is a novel human serine proteinase from seminal fluid. Purification, tissue distribution, and localization in prostate gland. Journal of Biological Chemistry, 269(29): 18843–8, 1994). The physiological function of prostasin, however, has remained unknown. By comparing gene expression of normal tissues, pre-invasive cancer, and invasive cancer, it would be highly advantageous to discover molecular markers that display a differential expression pattern between the pre-invasive and the invasive phenotypes and use these markers for a more precise diagnosis and prognosis of prostate and/or breast cancers. With the enhanced precision in diagnosis and prognosis, treatment options for patients with DCIS could then be stratified. Those with low risks of developing invasive breast cancer will have a higher confidence in choosing breast-conserving options, while those at high risks will ponder more aggressive options with the necessary follow-up treatments. Similarly, those males with low risks of developing invasive prostate cancer will have a higher confidence in choosing prostate-conserving options, while those at high risks will ponder more aggressive options with the necessary follow-up treatments.

SUMMARY OF THE INVENTION

The first objective of the present invention is to reduce deficiencies in the prior art with specific regard to differential diagnosis of invasive prostate and breast cancers and to treatment of invasive and metastatic prostate and breast cancers.

The second objective of the present invention is to provide a new marker for prostate and breast cancer.

The third objective of the invention is to provide as a drug to patients with carcinoma of the prostate via delivery of a functional prostasin gene.

The fourth objective of the invention is to provide as a drug to patents with carcinoma of the prostate via delivery of a functional prostasin cDNA.

The fifth objective of the invention is to provide as a drug to patents with carcinoma of the breast via delivery of a functional prostasin gene.

The sixth objective of the invention is to provide as a drug to patents with carcinoma of the breast via delivery of a functional prostasin cDNA.

This invention identifies prostasin serine protease as a potential marker, and as a tumor invasion suppressor for prostate and breast cancers and thus provides methods (a), (b), and (c) of determining invasiveness levels of human carcinomas:

(a) using prostasin protein levels, comprising the steps of: sampling a human carcinoma tissue; determining prostasin protein levels in the human carcinoma tissue; preferably by applying an immunological reagent-antibody to said tissue wherein the reagent-antibody becomes bound to prostasin protein in said tissue, and determining invasiveness of the human carcinoma tissue based on the prostasin protein levels; or (b) using prostasin mRNA levels, comprising the steps of: sampling a human carcinoma tissue; determining prostasin mRNA levels in the human carcinoma tissue preferably by applying prostasin-specific anti-sense RNA probes in an in situ hybridization to determine the prostasin mRNA levels in the separated human carcinoma tissue the determination of the prostasin mRNA levels in the separated human carcinoma sample tissue; to make possible and determining invasiveness of the human carcinoma tissue based on the prostasin mRNA levels; or (c) (c) using prostasin gene promoter DA methylation levels, comprising the steps of: sampling a human carcinoma tissue; determining prostasin gene promoter DNA methylation levels in the human carcinoma tissue, preferably by applying prostasin-promoter-specific oligonucleotide primers in a PCR to determine the prostasin gene promoter DNA methylation levels in the sampled human carcinoma tissue and determining invasiveness of the human carcinoma tissue based on the prostasin gene promoter DNA methylation levels, as well as a method of treating invasive human carcinomas comprising the steps of: incorporating human prostasin nucleic acid into a selected gene delivery vector nucleic acid to form a recombinant nucleic acid; preferably wherein the nucleic acid includes a gene or cDNA delivering the recombinant nucleic acid into a human carcinoma; and reducing invasiveness of the human carcinoma.

Further objects and advantages of this invention sill be apparent from the following detailed description of a presently preferred embodiment, which is illustrated schematically in the accompanying drawings.

DESCRIPTION OF THE PREFERRED EMBODIMENT

Before explaining the disclosed embodiment of the present invention in detail it is to be understood that the invention is not limited in its application to the details of the particular arrangement shown since the invention is capable of other embodiments. Also, the terminology used herein is for the purpose of description and not of limitation.

Using RT-PCR and western blot analyses, prostasin protein and mRNA expression were found in normal human prostate epithelial cells and the human prostate cancer cell line LNCaP, but discovered not present in the highly invasive human prostate cancer cell lines DU-145 and PC-3. Immunohistochemistry studies of human prostate cancer specimens revealed a down-regulation of prostasin in high-grade tumors.

Using RT-PCR and western blot analyses, prostasin protein and mRNA expression were found in a non-invasive human breast cancer cell line, MCF-7, while invasive human breast cancer cell lines MDA-MB-231 and MDA-MB-435s were also discovered not to express either the prostasin protein or the mRNA. A non-invasive human breast cancer cell line, MDA-MB-453, was shown to express prostasin mRNA but not prostasin protein. Examination of the prostasin gene promoter in the human prostate and breast cancer cell lines by Southern blot analysis revealed heterogeneous methylation of the promoter in DU-145, PC-3 and MDA-MB-453 cells, and homogeneous methylation of the promoter in MDA-MB-231 and MDA-MB-435s cells. The prostasin gene promoter in normal human prostate epithelial cells, the LNCaP and the prostasin gene promoter in the human prostate and breast cancer cell lines by Southern blot analysis revealed heterogeneous methylation of the promoter in DU-145, PC-3 and MDA-MB-453 cells, and homogeneous methylation of the promoter in MDA-MB-231 and MDA-MB-435s cells. The prostasin gene promoter in normal human prostate epithelial cells, the LNCaP and the MCF-7 cells was shown to be unmethylated. Transfection of DU-145 and PC-3 cells with a full-length human prostasin cDNA restored prostasin expression and reduced the in vitro invasiveness by 68% and 42%, respectively. Transfection of MDA-MB-231 and MDA-MB-435s cells with a full-length human prostasin cDNA restored prostasin expression and reduced the in vitro invasiveness by 50% for either cell line. Cell proliferation was unaffected by re-expression of prostasin. Our data indicate that prostasin is implicated in normal prostate biology and its down-regulation in prostate cancer, and its absence in invasive prostate and breast cancer cell lines indicates increased invasiveness. Our results also indicate that delivering a functional human prostasin gene to invasive prostate and breast cancers can reduce the invasiveness.

Figure 1:
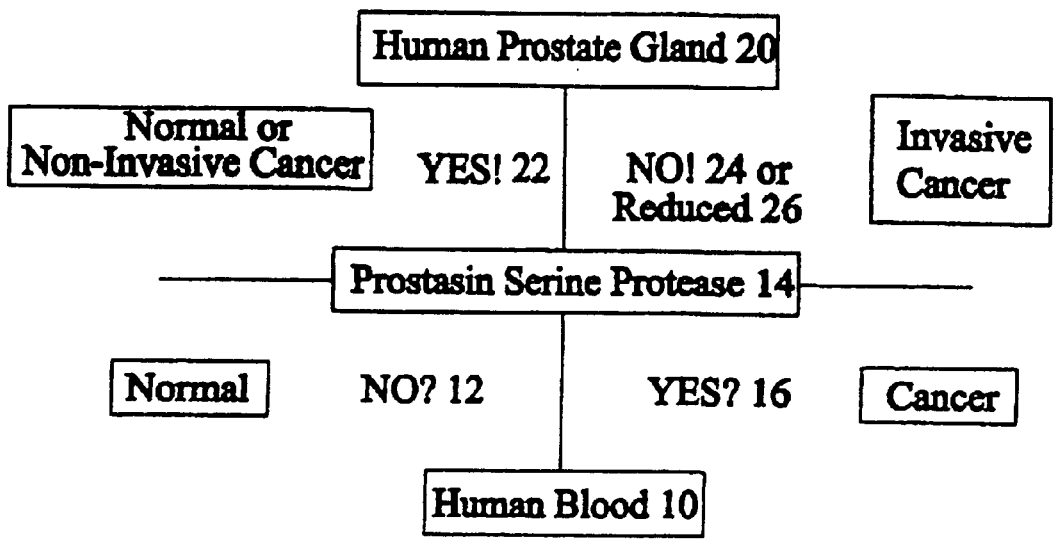
FIG. 1 is a diagrammatic representation of the analysis of prostasin indicative of the absence or existence, or of the invasiveness of human prostate carcinoma.
Figure 2:
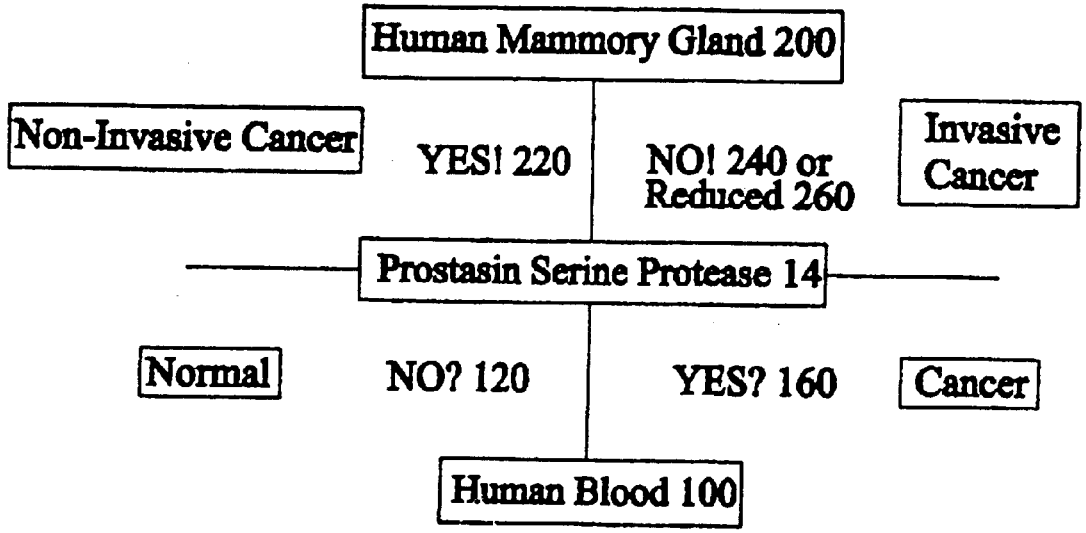
FIG. 2 is a diagrammatic representation of the analysis of prostasin indicative of the absence or existence, or of the invasiveness of human mammary carcinoma.

For a facile understanding of the invention embodied herein, reference should now be made to FIGS. 1 and 2. FIG. 1 sets forth a schematic for determining if a male has prostate cancer. Human blood 10 is taken from the male and analyzed for the presence of prostasin serine protease 14. If NO 12 prostasin is found, there is probably little or no cancer. If there is a presence YES 16 of prostasin serine protease 14, there is prostate cancer.

If a biopsy of the prostate gland 20 is analyzed for the presence of a normal amount YES 22 of prostasin serine protease 14, there is no cancer or there is non-invasive cancer. If there is NO 24 or Reduced 26 amount of prostasin serine protease 14, there is invasive cancer.

FIG. 2 sets forth a schematic for determining if a female has breast cancer. Human blood 100 is taken from the female and analyzed for the presence of prostasin serine protease 140. If NO 120 prostasin is found, there is prospectively no cancer. If there is a presence YES 160 of prostasin serine protease 140, there is breast cancer. If a biopsy of the breast 200 is analyzed for the presence of YES 220 of prostasin serine protease 140, there is no invasive cancer but may be non-invasive cancer. If there is NO 240 or Reduced 260 amount of prostasin serine protease 140, there is invasive cancer.

Figure 3:
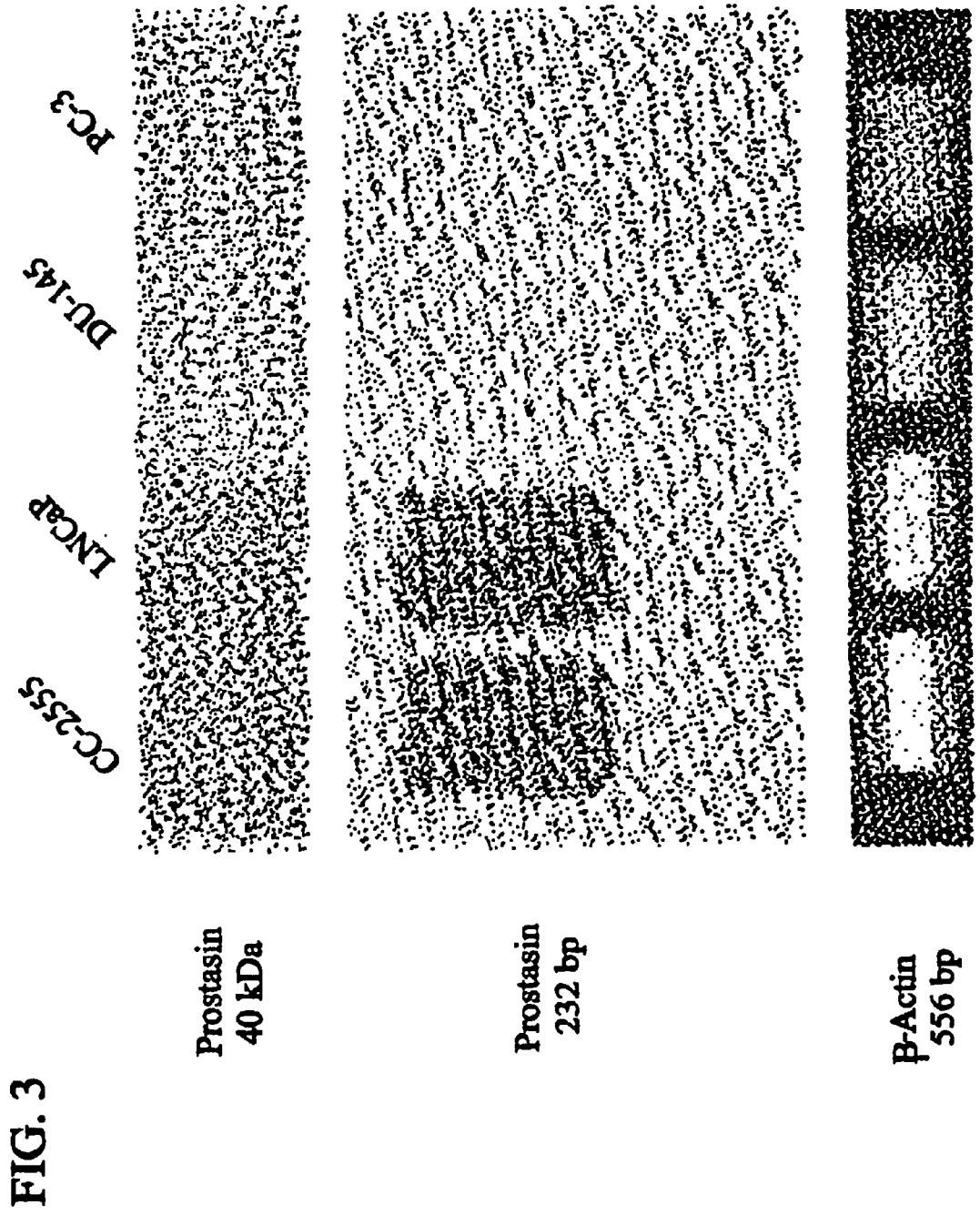
FIG. 3 shows human prostasin expression in prostate epithelial cells.

The levels of prostasin protein in the epithelial cells of the human prostate gland can be used as a diagnostic marker for the potential invasiveness of prostate tumors. The supporting evidence came from our findings that two invasive human prostate cancer cell lines DU-145 and PC-3 do not express prostasin while normal prostate epithelial cells and a non-invasive prostate cancer cell line LNCaP express both the prostasin mRNA and protein Refer now to FIG. 3 which shows human prostasin expression in prostate epithelial cells. By means of western blot analysis (upper panel), prostasin (as a 40-kDa band) was detected in normal human prostate epithelial cells (CC-2555) and the LNCaP cells, but not in the DU-145 or PC-3 cells. An equal amount of total protein (100 $\mu$g) was loaded for each sample. At the mRNA level, human prostasin mRNA (via a 232-bp amplified DNA band) was detected in normal prostate epithelial cells (CC-2555) and the LNCaP cells, but not in the DU145 or PC-3 cells as analyzed by RT-PCR/Southern blot hybridization (middle panel). Co-amplification of a 556-bp human $\beta$-actin message (as shown in the gel photograph in the lower panel) confirmed the quality and the quantity of the RNA applied in each RT-PCR.

Expression of prostasin protein is reduced in high-grade human prostate tumor. Prostatectomy specimens from 39 patients (128 sections) were subjected to immunohistochemistry using a prostasin-specific antibody. Overall, in non-tumor or benign prostate epithelia, 89.0% of the examined areas demonstrated positive staining for prostasin protein and 11.0% were considered negative (based on the scoring system used for HercepTest™, DAKO Corporation, Carpinteria, Calif.). In all tumor specimens that were examined, prostasin was detected in 93.3% of the low Gleason grade areas ($\leq$grade 2), 44.4% of Gleason grade 3 areas, 21.1% of Gleason grade 4 areas, but not in Gleason grade 5 areas (data summarized in Table 1). The mean prostasin immunostaining score was found significantly decreased in high-grade prostate tumors as compared to non-tumor areas (ANOVA, $p<0.0001$).

Representative staining images of non-tumor (benign) areas and prostate tumor areas are shown in FIGS. 4a–4l, which provides immunohistochemical detection of prostasin protein in tissues. Paraffin-embedded human prostate sections were stained for prostasin protein expression evaluation using a specific antibody as described (Yu J X, Chao L, Chao J. Prostasin is a novel human serine proteinase from seminal fluid. Purification, tissue distribution, and localization in prostate gland. Journal of Biological Chemistry, 269(29):18843–8, 1994). Prostasin positive staining (brown color) was detected in the cytoplasm and apical membrane in non-tumor or benign epithelial cells.

Figure 4A:
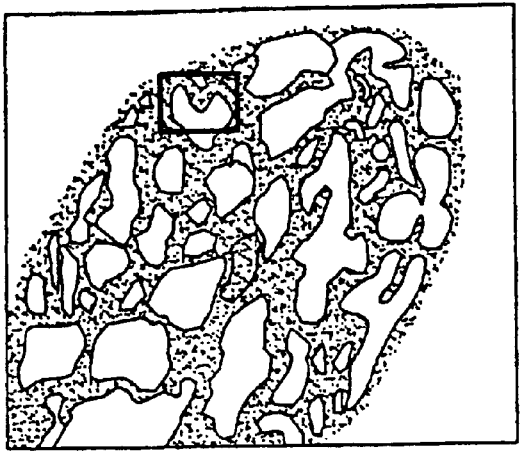
FIG. 4A shows immunohistochemical detection of prostasin protein in benign human prostate tissues.
Figure 4B:
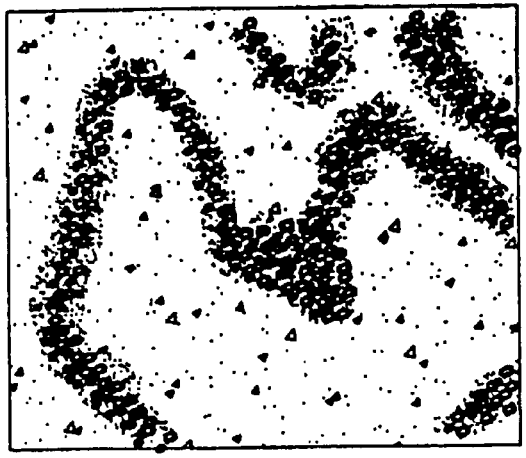
FIG. 4B is an enlarged view of the boxed region of FIG. 4A.
Figure 4C:
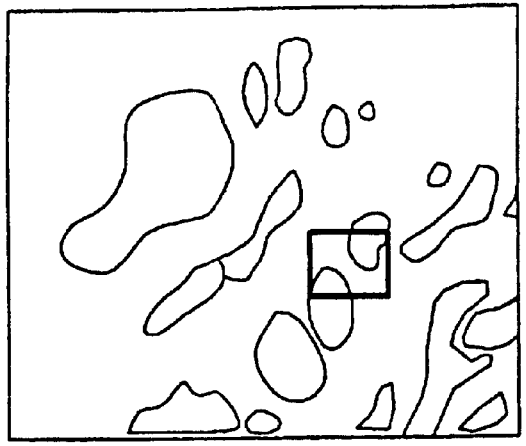
FIG. 4C shows immunohistochemistry of benign human prostate tissues with prostasin antibody omitted in the procedures, no epithelial cells displayed any staining.
Figure 4D:
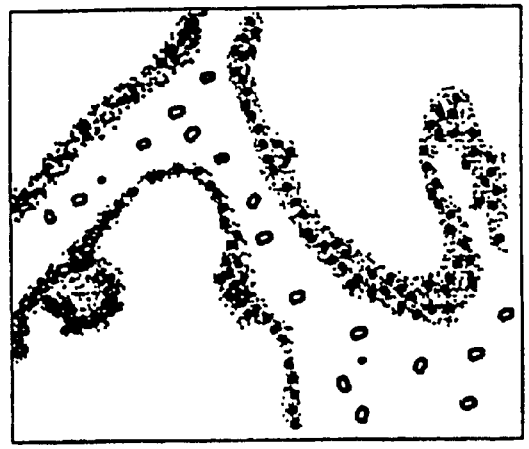
FIG. 4D is an enlarged view of the boxed region of FIG. 4C.
Figure 4E:
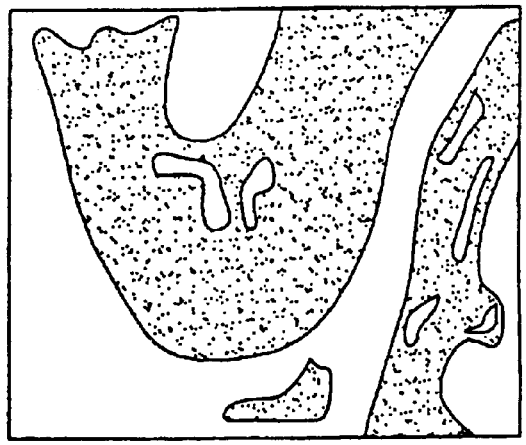
FIG. 4E shows immunohistochemistry of human prostate tumor with prostasin antibody omitted in the procedures, no epithelial cells displayed any staining.
Figure 4F:
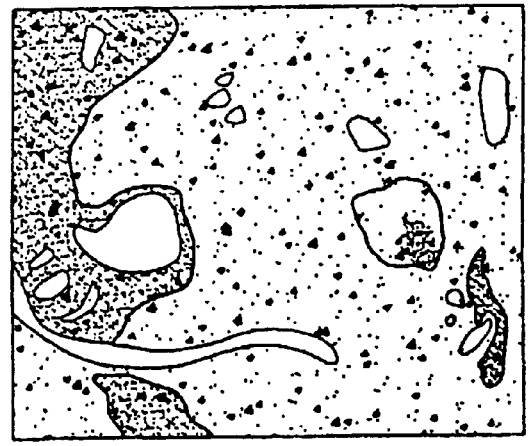
FIG. 4F shows immunohistochemical detection of prostasin protein in benign human prostate tissue surrounded by prostate carcinomas.
Figure 4G:
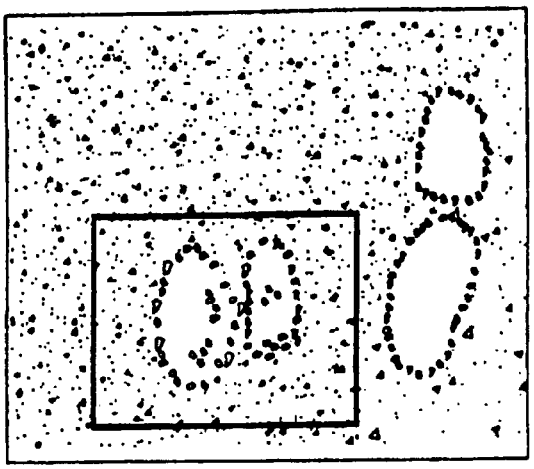
FIG. 4G shows immunohistochemical detection of prostasin protein in Gleason grade 2 prostate tumor.
Figure 4H:
FIG. 4H is an enlarged view of the boxed region of FIG. 4G.
Figure 4I:
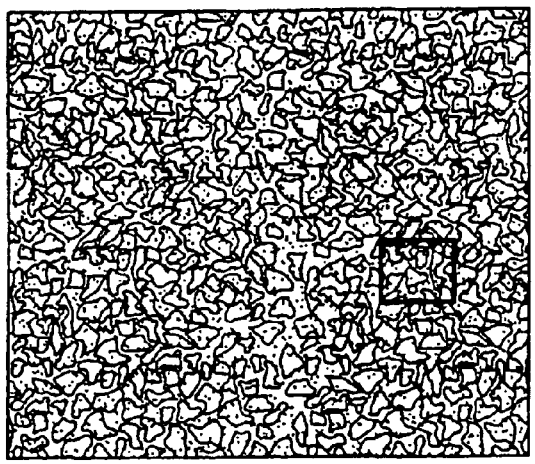
FIG. 4I shows immunohistochemical detection of prostasin protein in Gleason grade 3 prostate tumor.
Figure 4J:
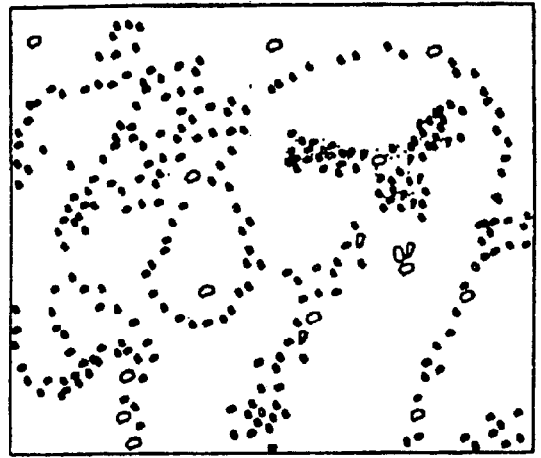
FIG. 4J is an enlarged view of the boxed region of FIG. 4I.
Figure 4K:
FIG. 4K shows immunohistochemical detection of prostasin protein in Gleason grade 4 prostate tumor.
Figure 4L:
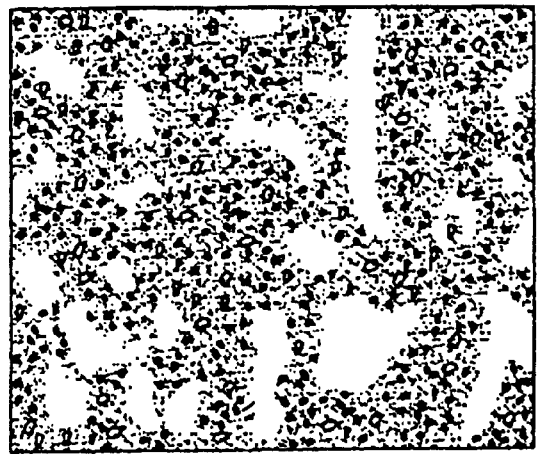
FIG. 4L is an enlarged view of the boxed region of FIG. 4K.

The prostasin protein was detected in the cytoplasm and on the plasma membrane (apical) of benign epithelial cells lining the secretory lumen as well as in the secretion inside the lumen (FIGS. 4A and 4B, score 3, or +++), confirming the results of (Yu J X, Chao L, Chao J. Prostasin is a novel human serine proteinase from seminal fluid. Purification, tissue distribution, and localization in prostate gland. Journal of Biological Chemistry, 269(29):18843–8, 1994). When a pre-immune rabbit serum was used in place of the prostasin antiserum, no stamina was observed in either the non-tumor epithelia (FIGS. 4C and 4D) or tumor epithelia (FIG. 4E). Tumor epithelia displayed various degree: of prostasin immunostaining as shown in FIGS. 4F–4L. In Gleason grade 1–2 tumors, moderate prostasin staining is seen in the cytoplasm and on the plasma membrane of some epithelial cells, as well as in the secretion in the lumen (FIGS. 4G and 4H, score 2, or ++). In Gleason grade 3 tumors, a lesser number of epithelial cells displayed the moderate level prostasin staining (FIGS. 4I and 4J). In Gleason grade 4 tumors, most epithelial cells did not show any prostasin staining, while some prostasin staining can be seen in rare, sporadic tumor cells (FIGS. 4K and 4L, as indicated by the arrow, score 0). Genetically, prostate tumors are heterogeneous and multi-focal in nature, in that one patient's grossanatomy tumor comes from multiple initial lesions which are caused by different initial transformation events and progress to different stages by different ensuing transformations (Isaacs J T, Bova G S. Prostate Cancer. In *The Genetic Basis of Human Cancer* (Eds. Vogelstein B and Kinzler K W), pp653–60, McGraw-Hill Health Professions Division, 1998). The Gleason grading, when used as a percentage of each cancer occupied by Gleason grade 4/5 areas, is independently associated with prostate cancer progression (Stamey T A, McNeal J E, Yemoto C M, Sigal B M, Johnstone I M. Biological determinants of cancer progression in men with prostate cancer. JAMA 281:1395–1400, 1999). We found a significant decrease of prostasin expression in the high-grade, i.e., the more progressively transformed tumors.

Figure 5:
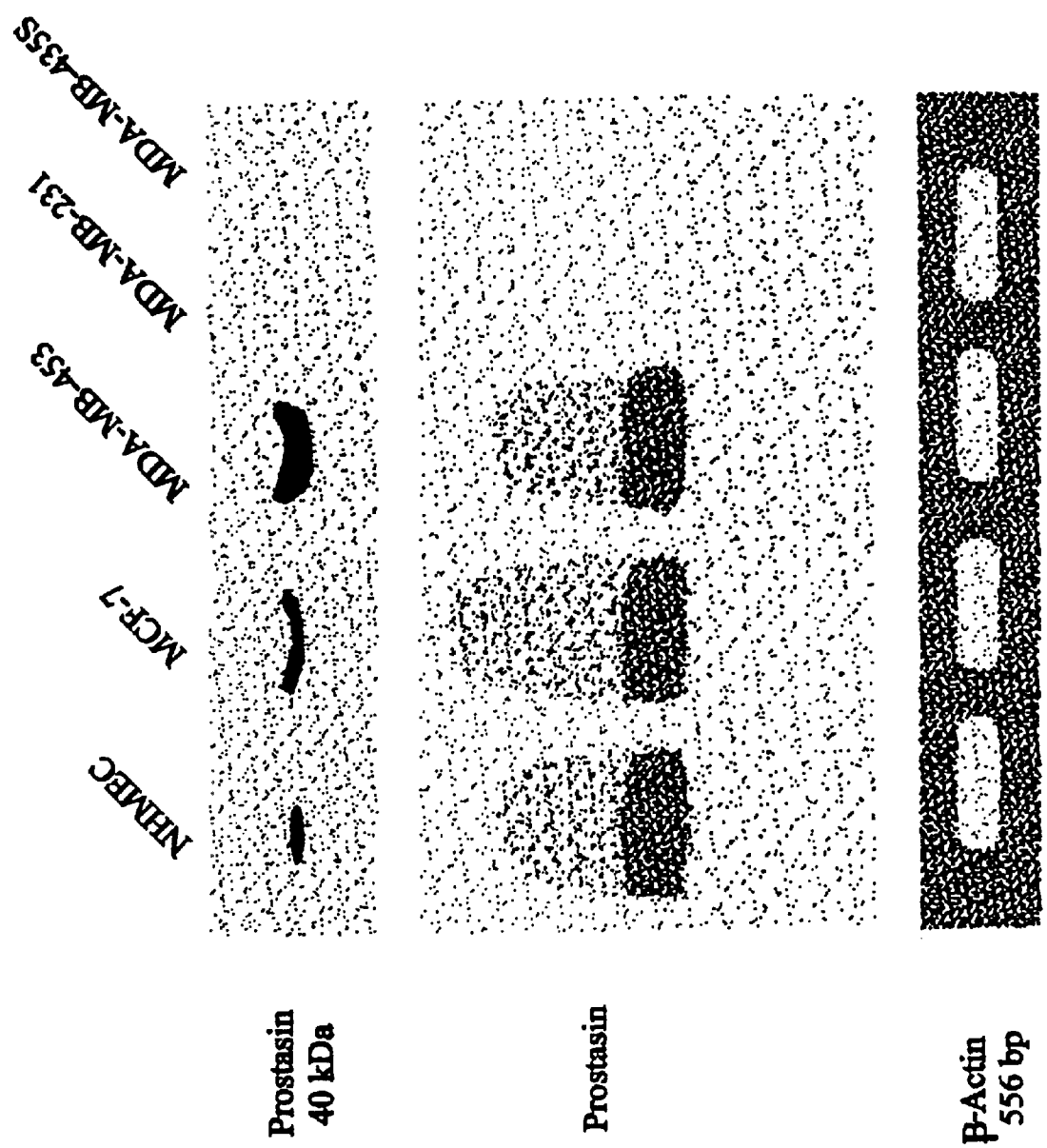
FIG. 5 shows human prostasin expression in human breast cancer cell lines.

As earlier indicated, FIG. 5 shows human prostasin expression in human breast cancer cell lines. By means of western blot analysis (upper panel), prostasin (as a 40-kDa band) was detected in MCF-7 cells, but not in MDA-MB-453, MDA-MB-231, or MDA-MB-435s cells. An equal amount of total protein (100 $\mu$g) was loaded for each sample. At the mRNA level, human prostasin mRNA (via a 232-bp amplified DNA band) was detected in MCF-7 and MDA-MB-453 cells, but not in the MDA-MB-231 or MDA-MB-435s cells as analyzed by RT-PCR/Southern blot hybridization (lower panel).

Prostasin mRNA expression is seen absent in two invasive human breast cancer cell lines while two non-invasive breast cancer cell lines express prostasin mRNA or protein. Analysis of prostasin expression in human breast cancer cell lines showed that the non-invasive MCF-7 and MDA-MB-453 cells express the prostasin mRNA while the highly invasive MDA-MB-231 and MDA-MB-435s cells do not express the prostasin mRNA (see FIG. 5). Expression of prostasin mRNA in normal human breast can be demonstrated by the presence of two GenBank™ normal human breast EST sequences coding for prostasin (Accession numbers R48653, and R48557). The MCF-7 cells also express the prostasin protein as determined by western blot analysis (again see FIG. 5).

Figure 6:
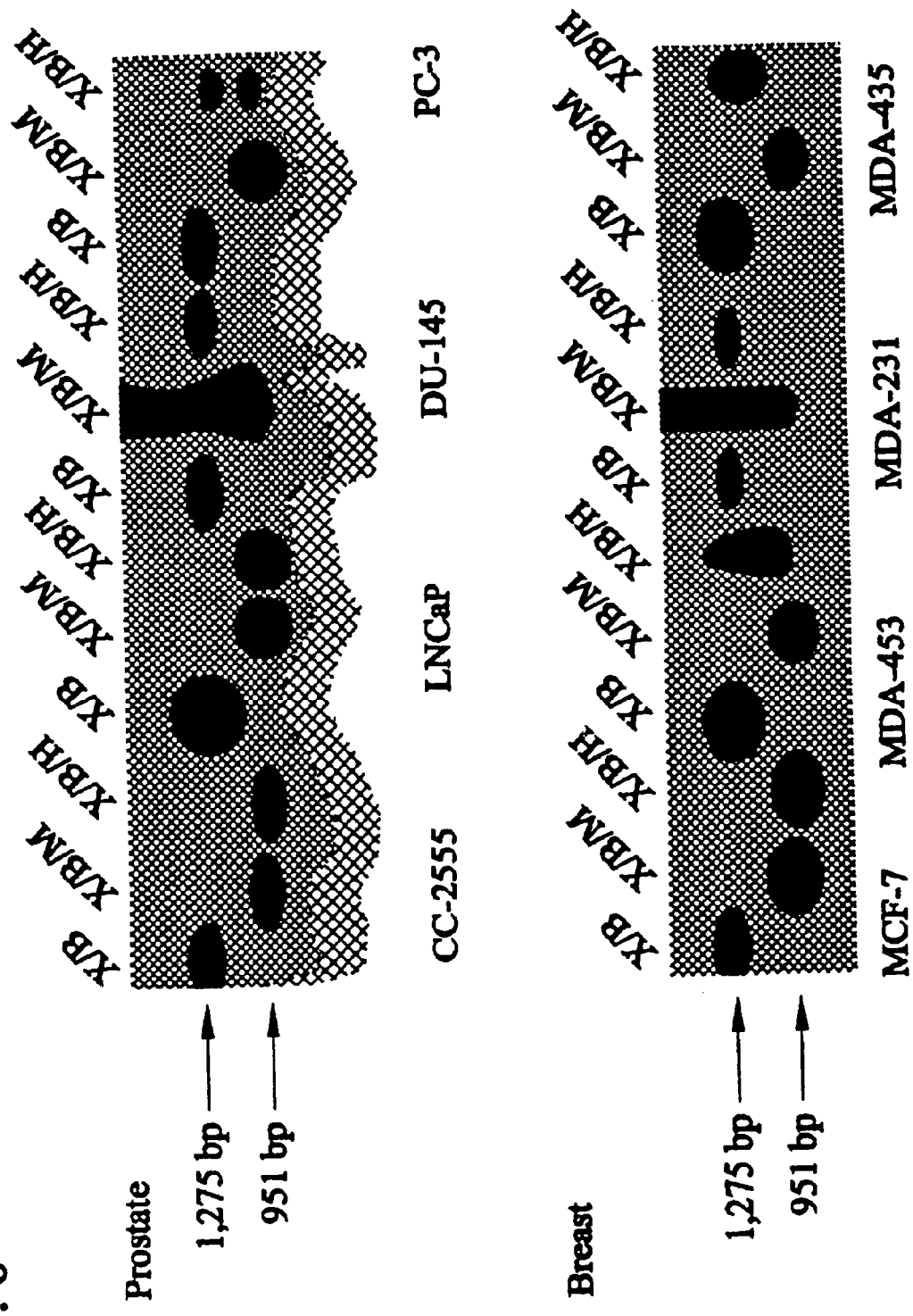
FIG. 6 shows promoter hypermethylation of the human prostasin gene in human prostate and breast cancer cell lines.

Prostasin down-regulation in prostate or breast cancer can be caused by promoter methylation or gene-specific mutation. Prostasin expression decreases with increasing prostate cancer grade and is absent in invasive prostate and breast cancer cell lines. The chromosomal locus where the human prostasin gene is, 16p11.2, however, is not known to be an LOH hot-spot in prostate cancer or in breast cancer. Epigenetic events (such as DNA methylation) may be an alternative mechanism of loss of expression for tumor suppressors or invasion suppressors. Refer now to FIG. 6 which shows promoter hypermethylation of the human prostasin gene in human prostate and breast cancer cell lines. Genomic DNA (5 $\mu$g) from the various cell lines (as indicated in the figure) were digested with the following restriction enzyme combinations. Xho I/BamH I (X/B, flanking cuts of the methylation-sensitive site), Xho I/BamH I/Msp I (X/B/M), or Xho I/BamH I/Hpa II (X/B/H). The digests were resolved in a 0.8% agarose gel and transferred to an Immobilon-N membrane for hybridization with a nick-translated prostasin promoter probe (bases 703–1469 of the prostasin gene sequence U33446). The probe detects a promoter fragment of 1,275 bp, which is cut by the methylation-insensitive enzyme Msp I to yield a 1,052-bp fragment for all DNA samples. The methylation-sensitive isoschizomer Hpa II yields the 1,052-bp fragment in the CC-2555 (normal prostate epithelial cells), the LNCaP, and the MCF-7 samples, indicating the hypomethylated or unmethylated state of the prostasin promoter in these cells. For DU-145, PC-3, and MDA-MB-453 DNA, both the 1,052-bp and the 1,275-bp fragments are generated in the methylation-sensitive digestion, suggesting incomplete methylation (one of two or more chromosomes) or clonal methylation in a sub-population of cells. For the MDA-MB-231 and MDA-MB-435, however, the Hpa II digestion did not yield the 1.052-bp but rather gave the 1,275-bp fragment. This homogeneous methylation pattern indicates that the Msp I/Hpa II site, at location-95 (relative to the transcription initiation site) of the prostasin promoter, is methylated (hypermethylated) in these DNA samples. Signal intensity variation may be attributed to aneuploidy.

An examination of the prostasin gene promoter region for DNA methylation differences among human prostate and breast cancer cell lines has been made,(see FIG. 6). We found that cells that express prostasin, normal prostate epithelial, LNCaP, and MCF7, are unmethylated in the prostasin promoter while MDA-MB-453 showed heterogeneous prostasin promoter methylation. For cells that do not express prostasin, DU-145 and PC-3 showed heterogeneous prostasin promoter methylation while MDA-MB-231 and MDA-MB-435 showed homogeneous hypermethylation in the promoter region of the prostasin gene.

Two human prostate cancer cell lines that do not express prostasin, the highly invasive DU-145 and PC-3, show heterogeneous methylation in the promoter region of the prostasin gene. The result suggests that at least one of the two (or more) chromosome 16's of these cell lines is methylated at the prostasin gene locus. The prostasin gene on the unmethylated chromosome may contain mutations that silenced the expression. An alternative explanation for the heterogeneous methylation pattern is that the methylation occurs in clonal cell populations, however, the lack of detectable prostasin mRNA in our RT-PCR-Southern blot analysis in the DU-145 and PC-3 cells argues against this possibility.

The significance of the finding on prostasin gene promoter hypermethylation in prostate or breast cancer is that the measurement of prostasin down-regulation as a cancer marker may be achieved by using a binary assay (yes-or-no), instead of a gradually decreasing quantity in the immuno-histochemistry assay (which is quite arbitrary).

Re-expression of human prostasin protein in invasive human prostate and breast cancer cells reduces invasiveness in vitro. At this point, reference should be made to FIG. 7 which shows the prostasin protein expression and in vitro invasive properties of the DU-145 and the PC-3 transfectants. DU-145 or PC-3 cells transfected with either a vector DNA (labeled as "vector") or a prostasin cDNA construct (labeled as "prostasin") were analyzed by a western blot analysis using a prostasin-specific antibody (upper panel) or subjected to an in vitro Matrigel chemoinvasion assay (lower panel) as described in (Liu D F, Rabbani S A. Induction of urinary plasmiinogen activator by retinoic acid results in increased invasiveness of human prostate cancer cells PC-3. Prostate, 21(5):269–76, 1995). The expressed human prostasin protein (a 40-kDa band) was detected in the prostasin cDNA-transfected DU-145 or PC-3 cells, but not in the vector-transfected cells. In the Matrigel chemoinvasion assay, the vector-transfected cells are expressed as being 100% invasive (solid bar), the open bar represents the relative invasiveness of the human prostasin cDNA-transfected cells. The data were analyzed by a Student t-test using the StatView software (Abacus Concepts, Inc., Berkeley, Calif.).

Figure 7:
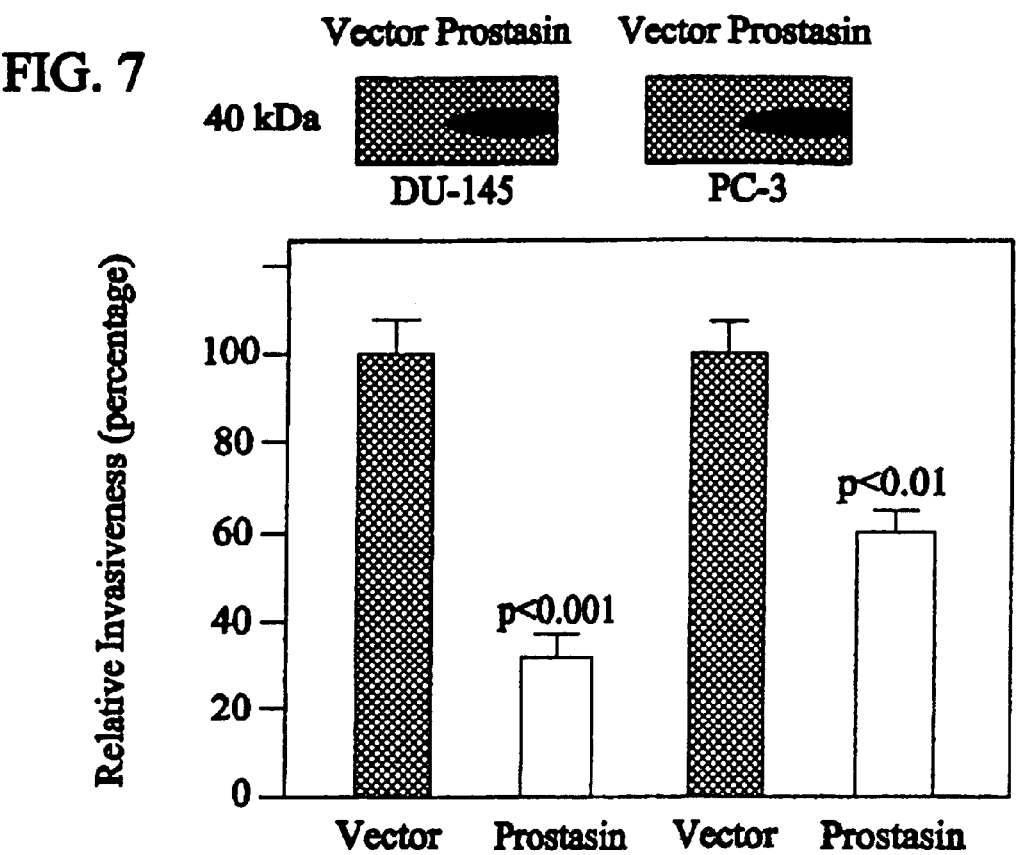
FIG. 7 shows prostasin protein expression and in vitro invasive properties of the DU-145 and the PC-3 transfectants.

It can be seen that Polyclonal DU-145 and PC-3 cells transfected with the human prostasin cDNA (designated DU-145/Pro, and PC-3/Pro, respectively) were confirmed to express the human prostasin protein, as shown in the western blot analysis of the cell lysate (FIG. 7, upper panel). The vector-transfected cells, designated DU-145/Vector or PC-3/Vector, respectively, were used as negative control in the western blot. A further examination of the DU-145/Pro and the PC-3/Pro cells by immunocytochemistry confirmed that 100% of the cells expressed the prostasin protein (data not shown). In in vitro Matrigel chemoinvasion assays (FIG. 7, lower panel), the invasiveness of DU-145/Pro cells was determined to be at 32% of that of DU-145. Vector cells (or, the reduction of invasiveness was at 68%). The invasiveness of PC-3/Pro cells was determined to be at 58% of that of PC-3/Vector cells (or, the reduction of invasiveness was at 42%). We performed in vitro cell proliferation assays on DU-145/Pro vs. DU-145/Vector cells, and on PC-3/Pro vs. PC-3/Vector cells, but did not observe any difference between the growth rates of the prostasin cDNA-transfected or the vector-transfected cells over an 8-day period (data not shown).

Figure 8:
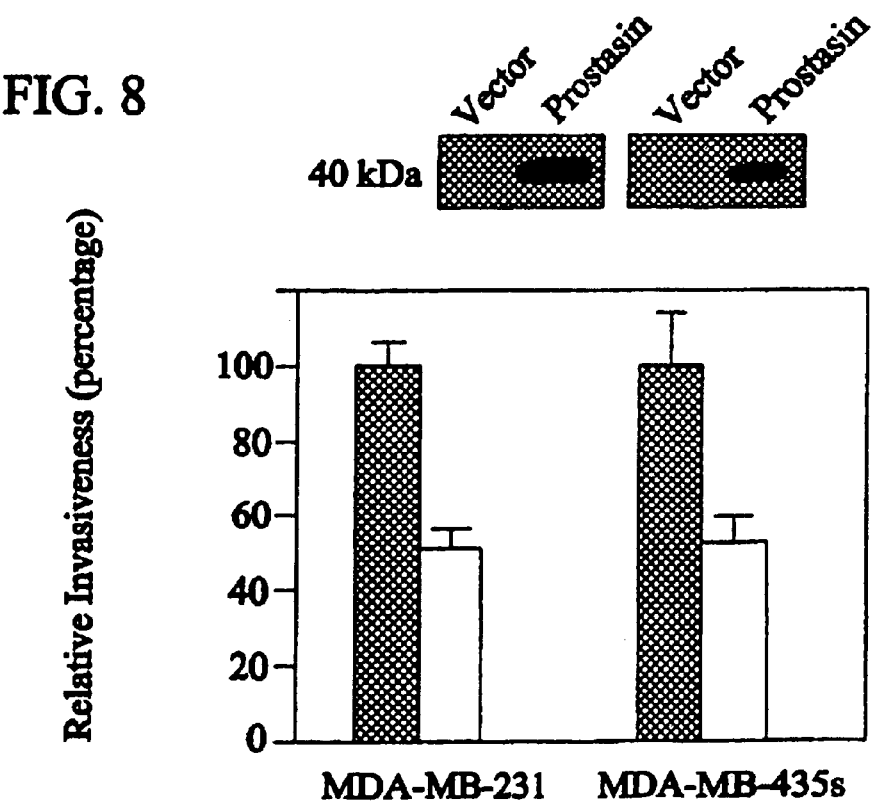
FIG. 8 shows prostasin protein expression and in vitro invasive properties of the MDA-MB-231 and the MDA-MB-435s transfectants.

Forced re-expression of human prostasin in two invasive human breast cancer cell lines reduced invasiveness. A full-length human prostasin cDNA under the control of an RSV promoter was transfected into the invasive breast cancer MDA-MB-231 and MDA-MB-435 cells. Reference should be made to FIG. 8 which shows prostasin protein expression and in vitro invasive properties of the MDA-MB-231 and the MDA-MB435s transfectants. MDA-MB-231 and MDA-MB-435s cells transfected with either a vector DNA (labeled as "vector") or a prostasin cDNA construct (labeled as "prostasin") were analyzed by a western blot analysis using a prostasin-specific antibody (upper panel) or subjected to an in vitro Matrigel chemoinvasion assay (lower panel) as referenced in (Liu D F, Rabbani S A. Induction of urinary plasminogen activator by retinoic acid results in increased invasiveness of human prostate cancer cells PC-3. Prostate, 27(5):269–76, 1995). The expressed human prostasin protein (a 40-kDa band) was detected in the prostasin cDNA-transfected MDA-MB-231 and MDA-MB-435s cells, but not in the vector-transfected cells. In the Matrigel chemoinvasion assay the vector-transfected cells are expressed as being 100% invasive (solid bar), the open bar represents the relative invasiveness of the human prostasin cDNA-transfected cells. The data were analyzed by a Student t-test using the StatView software (Abacus Concepts, Inc., Berkeley, Calif.).

Stable, polyclonal, episomal transfectants were obtained and the expression of human prostasin protein was confirmed by western blot analysis (FIG. 8, upper panel). In in vitro Matrigel chemoinvasion assays, the invasiveness of either cell lines expressing human prostasin was reduced by 50% as compared to the vector-transfected controls (FIG. 8, lower panel).

Taken together, the foregoing evidences linking prostasin level reduction or protasin absence to the invasiveness of prostate and breast cancer cell lines, or linking prostasin expression to reduced invasiveness. The evidence qualifies prostasin as an invasion suppressor, which thus is a marker for diagnosis of invasiveness of prostate and breast cancers, or as a therapeutic agent to treat invasive prostate and breast cancers.

Pathological grading by the Gleason system is performed after either surgery or biopsy, both highly invasive procedures, while blood tests such as that for the PSA prostate cancer marker can offer the hope of accurate diagnosis and prognosis without the harm of an invasive procedure. In practice, however, single markers suffer from an intrinsic limitation that the "positive" identifications are not always confirmed for the "diagnosed" disease. Biopsy is still required for a true positive identification of prostate cancer even in the case of the application of the PSA prostate cancer marker (Catalona W J, Partin A W, Slawin K M, Brawer M K, Flanigan R C, Patel A, Richie J P, deKernion J B, Walsh P C, Scardino P T, Lange P H, Subong E N, Parson R E, Gasior G H, Loveland K G, Southwick P C. Use of the percentage of free prostate-specific antigen to enhance differentiation of prostate cancer from benign prostatic disease: a prospective multicenter clinical trial [see comments]. JAMA, 279(19):1542–7, 1998). As stated above, it has been demonstrated in principle that many markers used in a multivariate approach may provide a highly accurate diagnosis (Greene G F, Kitadai Y, Pettaway C A, von Eschenbach A C, Bucana C D, Fidler I J. Correlation of metastasis-related gene expression with metastatic potential in human prostate carcinoma cells implanted in nude mice using an in situ messenger RNA hybridization technique. American Journal of Pathology 150(5):1571–82, 1997). From the standpoint of prostate cancer genetics, the multivariate approach is well supported by our current understanding. A serine protease structurally and genetically related to the PSA, the hK2 (human glandular kallikrein 2) has shown some promise of joining the list of markers applicable for prostate cancer diagnosis (Saedi M S, Hill T M, Kuus-Reichel K, Kumar A, Payne J, Mikolajczyk S D, Wolfert R L, Rittenhouse H G. The precursor form of the human kallikrein 2, a kallikrein homologous to prostate-specific antigen, is present in human sera and is increased in prostate cancer and benign prostatic hyperplasia. Clinical Chemistry, 44(10):2115–9, 1998). Structurally and in prostate gland biology, prostasin shares many common characteristics with both PSA and hK2, as being a secreted serine protease made in large abundance in prostate epithelial cells (Yu J X, Chao L, Chao J. Prostasin is a novel human serine proteinase from seminal fluid. Purification, tissue distribution, and localization in prostate gland. Journal of Biological Chemistry, 269(29):18843–8, 1994; Yu J X, Chao L, Chao J. Molecular cloning, tissue-specific expression, and cellular localization of human prostasin mRNA. Journal of Biological Chemistry, 270(22):13483–9, 1995). While high-grade prostate cancer cells produce less PSA protein than normal prostate cells or low-grade prostate cancer cells (Hakalahti L, Vihko P, Henttu P, Autio-Harmainen H, Soini Y, Vihko R. Evaluation of PAP and PSA gene expression in prostatic hyperplasia and prostatic carcinoma using northern-blot analyses, in situ hybridization and immunohistochemical stainings with monoclonal and bispecific antibodies. International Journal of Cancer, 55(4):590–7, 1; Sakai H, Yogi Y, Minami Y, Yushita Y, Kanetake H, Saito Y. Prostate specific antigen and prostatic acid phosphatase immunoreactivity as prognostic; Sakai H, Yogi Y, Minami Y, Yushita Y, Kanetake H, Saito Y. Prostate specific antigen and prostatic acid phosphatase immunoreactivity as prognostic), the serum PSA levels in prostate cancer patients increase due to tissue damage caused by invasive cancer (Rittenhouse H G, Finlay J A, Mikolajczyk S D, Partin A W. Human Kallikrein 2 (hK2) and prostate-specific antigen (PSA): two closely related, but distinct, kallikreins in the prostate. [Review] [457 refs] Critical Reviews in Clinical Laboratory Sciences, 35(4): 275–368, 1998). By comparison, we also believe prostasin is in the circulation of prostate cancer patients. As a result, a blood test for the circulating prostasin to indicate the presence and/or the stage of prostate cancer would be highly useful. (as illustrated in FIG. 1). In principal, the feasibility of a blood test based on prostasin detection to indicate cancer has been demonstrated by Berteau et al. (1999). These authors (Berteau P, Laribi Eschwege P, Lebars I, Dumas F, Benoit G, Loric S. Prostasin mRNA to detect prostate cells in blood of cancer patients. Clinical and Chemical Laboratory Medicine 37 (SS): S119, 1999), demonstrated a highly promising potential of using prostasin as a marker to detect circulating prostate epithelial cells, a sign of prostate tissue damage caused by invasive prostate cancer leading to the dissemination of prostate epithelial cells into the circulation. It is expected that a blood test for circulating prostasin to indicate the presence and/or the stage of breast cancer would be highly useful. (as illustrated in FIG. 2).

In summary of the invention, it has been taught herein that: protein prostasin as well as its MRA levels and its gene promoter DNA methylation levels can be used to determine the invasiveness level of human carcinomas; and, provide a method of treating invasive human carcinomas by delivery thereto of a recombinant nucleic acid formed by a human prostasin nucleic acid incorporated into a selected gene delivery vector. Those teachings are repeated for emphasis in the following:

1. Immunohistochemistry studies of human prostate cancer specimens revealed a down-regulation of prostasin in high-grade tumors.
2. Using RT-PCR and western blot analyses, prostasin protein and mRNA expression were found in a non-invasive human breast cancer cell line MCF-7, while invasive human breast cancer cell lines, MDA-MB-231 and MDA-MB-435s were found not to express either the prostasin protein or the mRNA. A non-invasive human breast cancer cell line, MDA-MB-453, was shown to express prostasin mRNA but not prostasin protein; and,
3. Examination of the prostasin gene promoter in the human prostate and breast cancer cell lines by Southern blot analysis revealed heterogeneous methylation of the promoter in DU-145, PC-3 and MDA-MB-453 cells, and homogeneous methylation of the promoter in MDA-MB-231 and MDA-MB-435s cells. The prostasin gene promoter in normal human prostate epithelial cells, the LNCaP and the MCF-7 cells was shown to be unmethylated. Transfection of DU-145 and PC-3 cells with a full-length human prostasin cDNA restored prostasin expression and reduced the in vitro invasiveness by 68% and 42%, respectively. Transfection of MDA-MB-231 and MDA-MB-435s cells with a full-length human prostasin cDNA restored prostasin expression and reduced the in vitro invasiveness by 50% for either cell line.

The preferred methods of separating sampled human carcinoma tissue from neighboring normal tissues is by laser capture micro-dissection.

While the invention has been described, disclosed, illustrated and shown in various terms of certain embodiments or modifications which it has presumed in practice, the invention is not intended to be, nor should it be deemed to be, limited thereby and such other modifications or embodiments as may be suggested by the teachings herein are particularly reserved especially as they fall within the breadth and scope of the claims here appended.

We claim:

1. A method of determining human prostate carcinomas non-invasiveness using prostasin MRNA levels, comprising the steps of:

sampling a human prostate carcinoma tissue;

determining prostasin mRNA levels in the human carcinoma tissue; and determining the human prostate carcinoma tissue is not invasive based on the prostasin mRNA levels.

2. The method of determining human prostate carcinomas non-invasiveness as in claim 1, wherein the step of determining prostasin mRNA levels includes the step of:

applying prostasin-specific oligonucleotide primers in an RT-PCR to determine the prostasin mRNA levels in the sampled human prostate carcinoma tissue.

3. The method of determining human prostate carcinomas non-invasiveness as in claim 1, wherein the step of determining prostasin mRNA levels includes:

applying prostasin-specific anti-sense RNA probes in an in situ hybridization to determine the prostasin mRNA levels in the sampled human carcinoma tissue.

4. A method of determining human breast carcinomas non-invasiveness using prostasin MRNA levels, comprising the steps of:

sampling a human breast carcinoma tissue;

determining prostasin mRNA levels in the human breast carcinoma tissue; and determining the human breast carcinoma tissue is not invasive based on the prostasin mRNA levels.

5. The method of determining human breast carcinomas non-invasiveness as in claim 4, wherein the step of determining prostasin mRNA levels includes the step of:

applying prostasin-specific oligonucleotide primers in an RT-PCR to determine the prostasin mRNA levels in the sampled human breast carcinoma tissue.

6. The method of determining human breast carcinomas non-invasiveness as in claim 4, wherein the step of determining prostasin mRNA levels includes the step of:

applying prostasin-specific anti-sense RNA probes in an in situ hybridization to determine the prostasin mRNA levels in the sampled human carcinoma tissue.

* * * * *